US00PP17332P2

(12) United States Plant Patent
Moore

(10) Patent No.: US PP17,332 P2
(45) Date of Patent: Jan. 2, 2007

(54) ***BUDDLEJA* PLANT NAMED 'MORNING MIST'**

(50) Latin Name: *Buddleja crispa×loricata*
Varietal Denomination: MORNING MIST

(76) Inventor: Peter Moore, 1 Valley View, Longstock, Stockbridg, Hants, SO20 6EF (GB)

( * ) Notice: Subject to any disclaimer, the term of this patent is extended or adjusted under 35 U.S.C. 154(b) by 44 days.

(21) Appl. No.: 11/123,554

(22) Filed: May 5, 2005

(51) Int. Cl.
*A01H 5/00* (2006.01)

(52) U.S. Cl. ..... Plt./242

(58) Field of Classification Search ..... Plt./242, Plt./226

See application file for complete search history.

*Primary Examiner*—Kent Bell
*Assistant Examiner*—Louanne Krawczewicz Myers

(57) ABSTRACT

A new cultivar of *Buddleja* named 'MORNING MIST' that is characterized by hardiness, compact habit, intensely silver leaves, and white flowers. In combination these traits set 'MORNING MIST' apart from all other existing varieties of *Buddleja* known to the inventor.

2 Drawing Sheets

Genus: *Buddleja*. Species: *crispa×loricata*.
Denomination: 'MORNING MIST'.

BACKGROUND OF THE INVENTION

The present invention relates to a new and distinct cultivar of butterfly bush that is grown for use as an ornamental shrub for the landscape. The new cultivar is known botanically as *Buddleja crispa×loricata* and will be referred to hereinafter by the cultivar name 'MORNING MIST'.

'MORNING MIST' resulted from a formal breeding program established by the inventor at his nursery in Stockbridge, United Kingdom. The inventor's nursery holds one of the United Kingdom National Collections of the genus *Buddleja* which have been approved by The National Council for the Preservation of Plants and Gardens (N.C.C.P.G.). The inventor's nursery maintains a reference collection of over one hundred cultivars and species of the genus *Buddleja*.

The purpose of the breeding program was to produce a hardy silver-leaved *Buddleja*. The inventor proceeded as follows:

In 1994, the inventor selected from the National Collection an unnamed plant of the species *Buddleja crispa* (unpatented) as prospective female parent for deliberate cross-pollination with an unnamed plant of the species *Buddleja loricata* (unpatented) as male parent.

*Buddleja crispa* is a silver-gray foliaged drought-tolerant shrub which is native to the lower slopes of the southern Himalayas. *Buddleja loricata,* also known as mountain sagewood, is native to the higher altitudes, typically above 1800 meters, of the eastern cape of South Africa and KwaZulu-Natal.

To conduct the hybridization the inventor first removed the anthers on the female parent. Then carefully obtaining pollen from the male parent, the inventor placed the pollen on the style of the female parent flowers. The inventor protected the flowers by covering them with pollinating bags to prevent cross-pollination from plants other than the specified parents. The seed that resulted from this hybridization was collected by the inventor in the fall of 1994 and sown by the inventor in the spring of 1995. The inventor planted the resulting seedlings into an open ground bed in the fall of 1995 in order to be able to evaluate them over the ensuing years for certain desirable characteristics.

By 1997, the inventor selected a single plant from the seedling bed for its unique characteristics and combination of intensely silvered foliage and compact, well-branched growth habit. This single plant is the subject of the present invention, 'MORNING MIST'.

'MORNING MIST' is an individual whole plant hybrid that resulted from the cross-pollination of the female parent, a plant of the species *Buddleja crispa* (unnamed, unpatented) and the male parent, a plant of the species *Buddleja loricata* (unnamed, unpatented).

The distinguishing traits of 'MORNING MIST' are evergreen foliage, hardiness, white flowers, compact habit, and leaves that are intensely silver in color. The cultural requirements for 'MORNING MIST' are well-drained soil, full sun, and moderate water. 'MORNING MIST' exhibits no pest or disease problems known to the inventor.

The closest comparison plants known to the inventor are the parents *Buddleja crispa* and *Buddleja loricata.* Whereas 'MORNING MIST' and *Buddleja crispa* each have silvered foliage, the color of the flowers of *Buddleja crispa* varies between pink, lilac and purple. The flowers are carried in long sparse panicles. *Buddleja loricata* exhibits medium to dark green foliage and flowers which are sweetly scented and colored creamy white or yellow, with orange centers. Thus, 'MORNING MIST' is distinguishable from the comparison plants by its white flowers and intensely silver colored foliage.

The first asexual propagation of 'MORNING MIST' was conducted by the inventor in 1998 in Stockbridge, United Kingdom. The method of propagation used was softwood cuttings. Since that time, under careful observation, the distinguishing characteristics have been determined stable, uniform and true to type in successive generations.

The inventor has filed an application for a grant of European Community Plant Breeders Rights, serial number 2003/0022, filed Oct. 6, 2003.

The first public sale or distribution of plants of 'MORNING MIST' took place by the inventor at the inventor's nursery in July 2004.

SUMMARY OF THE INVENTION

The following represent the distinguishing characteristics of the new *Buddleja crispa×loricata* cultivar 'MORNING MIST'. In combination these traits set 'MORNING MIST' apart from all other existing varieties of *Buddleja* known to the inventor. 'MORNING MIST' has not been tested under all possible conditions and phenotypic differences may be observed with variations in environmental, climatic, and cultural conditions, however, without any variance in genotype.

1. 'MORNING MIST' is evergreen.
2. 'MORNING MIST' exhibits white flowers.
3. 'MORNING MIST' is asexually propagated using softwood cuttings.
4. 'MORNING MIST' exhibits compact habit.
5. 'MORNING MIST' exhibits foliage that is intensely silver in color.
6. 'MORNING MIST' is 1.5 to 2 meters in height and 1.5 to 2 meters in width at maturity.
7. The cultural requirements of 'MORNING MIST' are well-drained soil, full sun, and moderate water.
8. 'MORNING MIST' is an ornamental shrub suitable for use as a container plant, herbaceous border or shrub border plant for the landscape.
9. The woolly stems and foliage of 'MORNING MIST' can be used in cut flower arrangements.
10. 'MORNING MIST' is hardy to minus 10° Centigrade.

BRIEF DESCRIPTION OF THE DRAWINGS

The accompanying color drawings FIG. 1 and FIG. 2 illustrate and are taken from plants which are in their second year of growth from a single cutting. The plants have been grown out-of-doors in Hampshire, England.

The drawing labeled FIG. 1 illustrates a single plant of 'MORNING MIST' just coming into bud.

The drawing labeled FIG. 2 illustrates a close-up view of the inflorescence of 'MORNING MIST'. FIG. 1 and FIG. 2 were made using conventional techniques and although foliage colors may appear different from actual colors due to light reflectance, they are as accurate as possible by conventional photography.

BOTANICAL DESCRIPTION OF THE PLANT

Figure 1:
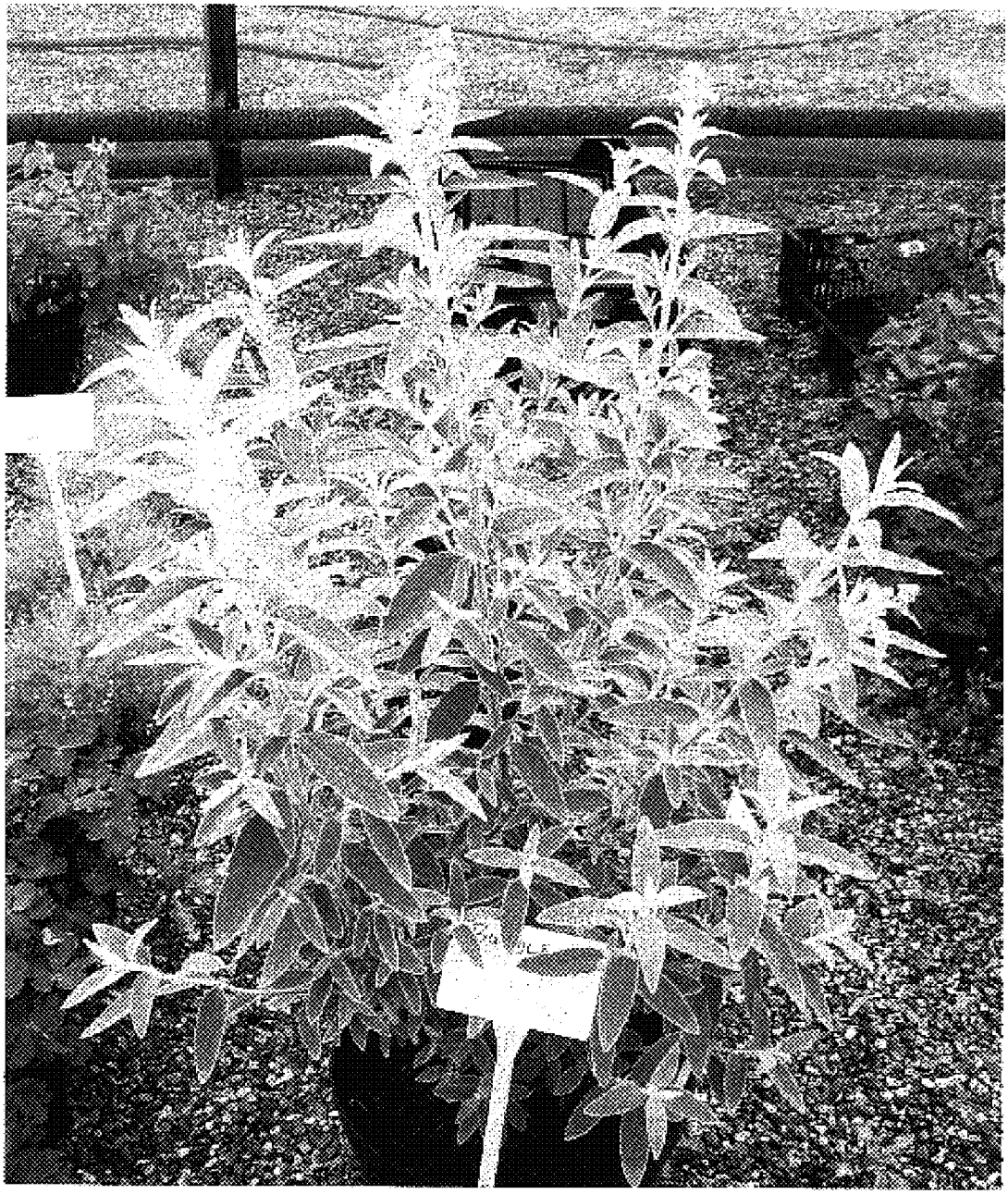
FIG. 1 and FIG. 2 illustrate the overall appearance of the new *Buddleja* cultivar 'MORNING MIST', showing the colors as true as it is reasonably possible to obtain in colored reproductions of this type. Colors in the drawings may differ from the color values cited in the detailed botanical description, which accurately describe the actual colors of the new variety 'MORNING MIST'.
Figure 2:
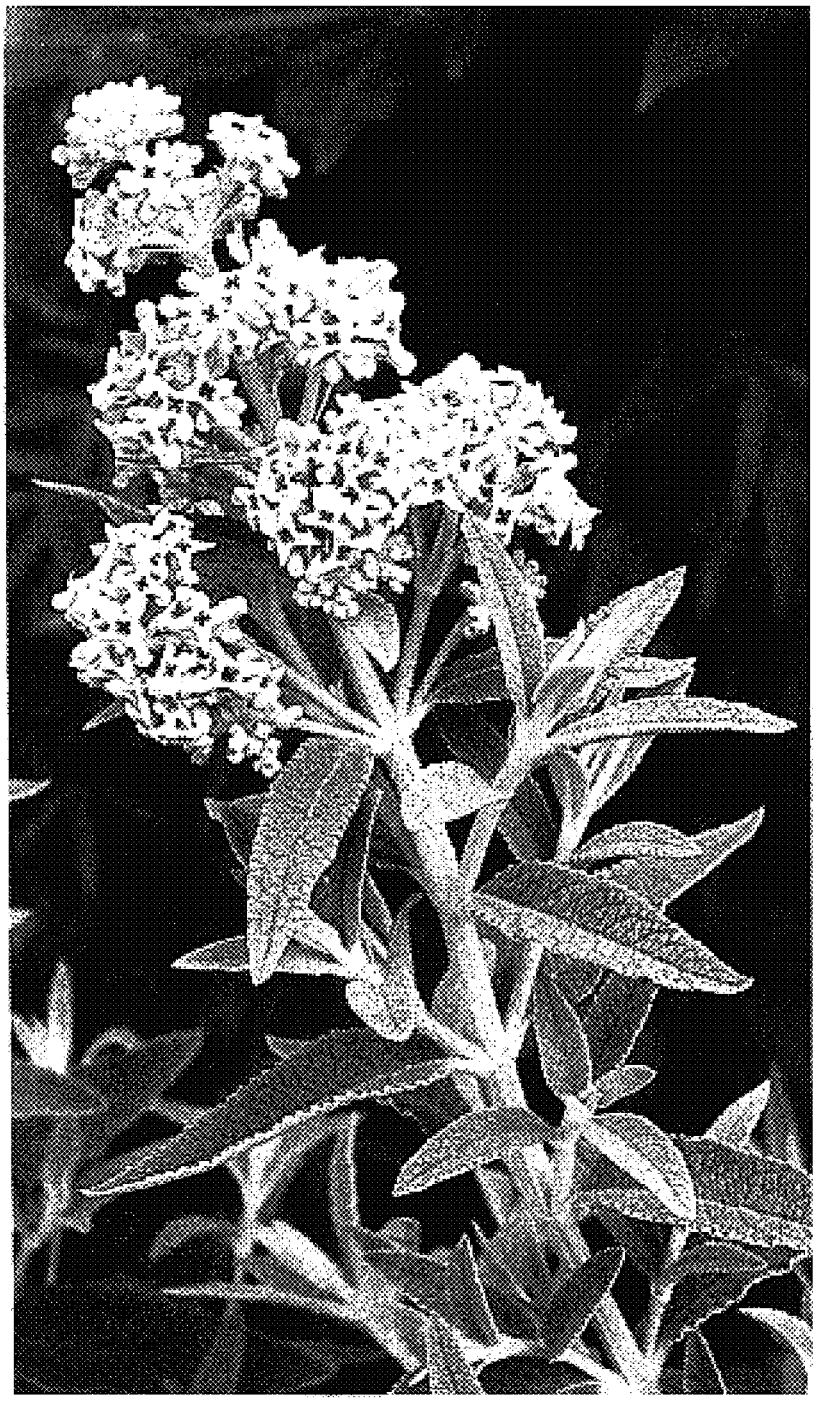

The following is a detailed description of the *Buddleja* cultivar named 'MORNING MIST'. Data was collected in Arroyo Grande, Calif. from 9-month-old plants that were grown out-of-doors. Color determinations are in accordance with 2001 edition of Colour Chart of The Royal Horticultural Society, London, England, except where general color terms of ordinary dictionary significance are used.

Botanical classification: *Buddleja crispa×loricata* 'MORNING MIST'.
Genus: *Buddleja.*
Species: *crispa×loricata.*
Denomination: 'MORNING MIST'.
Commercial classification: Shrub.
Common name: Butterfly bush.
Type: Ornamental.
Uses: Patio container plant, herbaceous border or shrub border plant for the landscape. Stems and foliage can be used in cut flower arrangements.
Container size: Suggested size is 1-liter commercial container.
Cultural requirements: Well-drained soil, full sun, and moderate water.
Parentage: 'MORNING MIST' is a hybrid that resulted from the cross-pollination of the following parent plants:
- *Seed parent.*—An unnamed plant of the species *Buddleja crispa.*
- *Pollen parent.*—An unnamed plant of the species *Buddleja loricata.*

Plant description:
- *Blooming seasons.*—Spring and summer.
- *Vigor.*—Low vigor.
- *Plant habit.*—Compact habit.
- *Height in maturity.*—1.5 to 2 meters in height at maturity.
- *Width at maturity.*—1.5 to 2 meters in width at maturity.
- *Hardiness.*—Hardy to minus 10° Centigrade.

Propagation: Propagation is accomplished using the method of softwood cuttings.
- *Root system.*—Fibrous.
- *Time to initiate rooting.*—3–4 weeks are needed to produce roots on the initial cuttings.
- *Temperature to initiate rooting.*—The ideal air temperature for rooting under greenhouse conditions is 20° Centigrade.
- *Crop time.*—9–12 months are needed to produce a commercial 1-liter container plant from an initial cutting.
- *Seasonal interest.*—White flowers in spring and summer.
- *Disease and pest susceptibility or resistance.*—No susceptibility or resistance to any particular disease or pest has been observed by the inventor.
- *Special growing requirements.*—Hard pruning in early spring of each year encourages and maintains a compact and attractive plant form with more profuse flowering later in the season.

Stem:
- *Stem diameter.*—0.50 cm. in diameter.
- *Stem length.*—Stems are an average of 45 cm. in length on an individual plant.
- *Stem shape.*—The cross-section of stems is flattened oval in shape.
- *Stem surface.*—Flocculent.
- *Pubescence.*—Present.
- *Pubescence color.*—196D.
- *Stem color.*—Individual colors 166A and 196D are present on an individual stem.
- *Internodes.*—2.75 cm. between nodes.

Foliage:
- *Type.*—Evergreen.
- *Leaf arrangement.*—Combination of opposite and whorled.
- *Leaf division.*—Simple.

*Leaf shape.*—Lanceolate.
*Leaf base.*—Attenuate.
*Leaf apex.*—Acute.
*Leaf venation.*—Anastomose.
*Vein color* (*abaxial surfaces*).—196D.
*Vein color* (*adaxial surfaces*).—148B.
*Leaf surfaces* (*adaxial surfaces*).—Pubescent and slightly rugose.
*Leaf surfaces* (*abaxial surfaces*).—Flocculent.
*Leaf margins.*—Crenate and crisped.
*Leaf attachment.*—Petiolate.
*Petiole dimensions.*—3 mm. in length and 3 mm. in width.
*Petiole shape.*—Sulcate.
*Petiole color.*—189D.
*Petiole surface.*—Flocculent.
*Leaf color* (*adaxial surfaces*).—There are both individual leaves that are 148B, and individual leaves that are 194B on an individual plant.
*Leaf color* (*abaxial surfaces*).—196D.
*Leaf texture* (*abaxial surfaces*).—Woolly texture.
*Leaf texture* (*adaxial surfaces*).—Felted texture.
*Leaf length.*—Leaves range from 4 to 8 cm. in length on an individual plant.
*Leaf width.*—Leaves range from 1 to 2.5 cm. in width on an individual plant.
*Average number of leaves per stem.*—An average of 44 leaves per individual stem.
*Foliar fragrance.*—Slight sage-like scent.

Flower:
*Inflorescence.*—Terminal panicle.
*Petals.*—Four in number.
*Fused or unfused.*—Basally fused.
*Petal margin.*—Entire.
*Petal apex.*—Rounded.
*Petal base.*—Truncate.
*Petal surfaces* (*adaxial surfaces*).—Pubescent.
*Petal surfaces* (*abaxial surfaces*).—Flocculent.
*Color of pubescence* (*abaxial and adaxial surfaces*).—158D.
*Petal shape.*—Rotund.
*Petal dimensions.*—3 mm. in width and 3 mm. in length.
*Petal color* (*adaxial surfaces*).—158D.
*Petal color* (*abaxial surfaces*).—158D.
*Aspect.*—Facing upward.
*Flower shape.*—Salverform.
*Flower color* (*adaxial surface*).—158D.
*Flower color* (*abaxial surface*).—158D.
*Flower changes as bloom period ends* (*abaxial and abaxial surfaces*).—Color changes to 165B.
*Corolla tube color* (*inside surface*).—167A.
*Corolla tube color* (*outer surface*).—158D.
*Corolla tube surfaces* (*inner and outer surfaces*).—Pubescent.
*Color of pubescence* (*inner and outer surfaces*).—158D.
*Corolla tube length.*—3 mm. in length.
*Corolla tube shape.*—Tubular in shape.
*Corolla tube diameter.*—2 mm. in diameter.
*Color of peduncle.*—196D.
*Peduncle surface.*—Flocculent.
*Peduncle length.*—1.50 cm. in length.
*Peduncle diameter.*—2 mm. in diameter.
*Peduncle shape.*—Flattened oval in cross-section.
*Pedicel dimensions.*—5 mm. in length and 2 mm. in diameter.
*Pedicel color.*—196D.
*Pedicel shape.*—Flattened oval in cross-section.
*Pedicel surface.*—Flocculent.
*Flowers persistent or self-cleaning.*—Flowers are persistent.
*Lastingness of the overall inflorescence.*—3 to 4 weeks.
*Lastingness of an individual flower.*—7 to 9 days.
*Dimensions of inflorescence.*—8.5 cm. in height and 6.75 cm. in diameter.
*Dimensions of panicle.*—25 mm. in length and 25 mm. in diameter.
*Dimensions of flower.*—7 mm. in depth and 5 mm. in diameter.
*Quantity of flowers.*—Quantity ranges from 50–60 individual flowers to an individual inflorescence.
*Bud color.*—155B.
*Bud apex.*—Rounded.
*Bud surface.*—Flocculent.
*Bud shape.*—Globose.
*Bud dimensions.*—3 mm. in length and 2.75 mm. in width.
*Calyx dimensions.*—3 mm. in width and 4 mm. in length.
*Calyx shape.*—Tubular.
*Sepals.*—Four in number.
*Sepal shape.*—Lanceolate.
*Sepal dimensions.*—4 mm. in length and 1.75 mm. in width.
*Sepal apex.*—Acute.
*Sepal margin.*—Entire.
*Sepal surface.*—Flocculent.
*Sepal color* (*both upper and lower surfaces*).—196D.
*Flower fragrance.*—Slight sage-like scent.

Reproductive organs:
*Stamens.*—Four in number adnate to inside surface of corolla tube.
*Stamen dimensions.*—3 mm. in length and less than 1 mm. in diameter.
*Stamen color.*—163A.
*Anther dimensions.*—1 mm. in length and 0.50 mm. in diameter.
*Anther shape.*—Oblong.
*Anther color.*—163D.
*Pollen.*—None observed.
*Pistil.*—One in number.
*Pistil shape.*—Filament.
*Pistil dimensions.*—4 mm. in length and 0.75 mm. in diameter.
*Pistil color.*—144D.
*Stigma color.*—144A.
*Style color.*—144D.
*Ovary.*—Present.
*Ovary position.*—Superior.
*Ovary shape.*—Oval.
*Ovary dimensions.*—1.50 mm. in height and 1 mm. in diameter.
*Ovary surface.*—Flocculent.

Seed: No seed has been observed.

It is claimed:

1. A new and distinct variety of *Buddleja* plant named 'MORNING MIST' as described and illustrated.

* * * * *